(12) United States Patent
Koteskey (10) Patent No.: US 8,261,622 B2
(45) Date of Patent: Sep. 11, 2012

(54) SYSTEM FOR SAMPLING SLUDGE

(75) Inventor: Gary L. Koteskey, Boyne City, MI (US)

(73) Assignee: GAG/Sim-Tech Filters, Inc., Boyne City, MI (US)

( * ) Notice: Subject to any disclaimer, the term of this patent is extended or adjusted under 35 U.S.C. 154(b) by 385 days.

(21) Appl. No.: 12/534,917

(22) Filed: Aug. 4, 2009

(65) Prior Publication Data

US 2010/0071485 A1 Mar. 25, 2010

Related U.S. Application Data

(60) Provisional application No. 61/100,045, filed on Sep. 25, 2008.

(51) Int. Cl.
*G01N 1/12* (2006.01)
(52) U.S. Cl. ..................................... 73/864.65
(58) Field of Classification Search ............... 73/864.65
See application file for complete search history.

(56) References Cited

U.S. PATENT DOCUMENTS

| | | | |
|---|---|---|---|
| 4,580,454 A | 4/1986 | Deja | 73/864.63 |
| 4,594,905 A | 6/1986 | Roberts | 73/864.63 |
| 5,031,469 A | 7/1991 | Blackburn et al. | 73/864.63 |
| 5,104,625 A | 4/1992 | Kenney | 422/100 |
| 5,113,711 A | 5/1992 | Davloor et al. | 73/864.63 |
| 5,179,859 A | 1/1993 | Van Niekerk | 73/864.64 |
| 5,209,129 A | 5/1993 | Jaselskis et al. | 73/864.64 |
| 5,445,038 A | 8/1995 | Hueller | 73/864.63 |
| 5,922,975 A | 7/1999 | Butler et al. | 73/864.74 |
| 6,811,692 B2 | 11/2004 | Koteskey | 210/238 |

OTHER PUBLICATIONS

Simple Tools Used to Measure Septic Tank Floating Scum Thickness and Sludge Level in the Septic Tank, downloaded May 18, 2012, pp. 1-5, available at http://inspectapedia.com/septic/Septic_Tank_Measuring_Tool.htm.
How to Operate and Maintain Septic Tank/Soil-Absorption Systems, Sep. 1982, pp. 1-12, United States Department of Agriculture, available at http://www.fs.fed.us/t-d/pubs/pdfimage/82711302.pdf.

*Primary Examiner* — Hezron E Williams
*Assistant Examiner* — Rodney T Frank
(74) *Attorney, Agent, or Firm* — Brinks Hofer Gilson & Lione (57) ABSTRACT

A device and method for sampling a fluid, especially a fluid of varying densities, are provided. The device includes a retention tube configured to receive a sample of the fluid, and can include a support jacket to support the retention tube. A control member is positioned within the retention tube with a plug attached to the distal end. The plug is movable away from the opening to facilitate laminar flow of the fluid into the retention tube. The plug can sealably engage the retention tube by affixing a portion of the control member. The device can be jolted to cause the control member to stretch, which disengages the plug temporarily, thereby releasing a lab sample portion from the retention tube. The rest of the sample of fluid can be released by completely releasing the plug from sealing contact.

16 Claims, 9 Drawing Sheets

SYSTEM FOR SAMPLING SLUDGE

CROSS REFERENCE TO RELATED APPLICATION

This application is related to and claims all available benefit of U.S. Provisional Application No. 61/100,045, filed Sep. 25, 2008, which is incorporated herein by reference in its entirety.

BACKGROUND

1. Field of the Invention

This invention generally relates to a sampling device adapted to be immersed in a body of fluid for extracting therefrom a sample. More particularly, this invention relates to a sampling device adapted to be immersed in a body of fluid for extracting therefrom a core sample including regions of varying density, such as any combination of scum, liquid and sludge.

2. Background of the Invention

It is often desirable to obtain a sample of fluid from tanks, drums, and other containers in order to analyze its contents for assurance that the system is performing satisfactorily or for environmental concerns, such as if the fluid is toxic, dangerous, or undesirable. Typical applications requiring such samples can include waste water/fresh water sampling, septic tank sampling, well sampling and other situations where the collection of a sample with roughly a small percentage of solids is needed. The fluid to be sampled can have one or more layers of diverse densities, generally called scum, liquid, sludge or the like.

One of the challenges of taking such samples is to obtain a sample that accurately represents the exact make-up of the fluid as close as possible from top and to bottom layers. Generally, the sampler device used to obtain such sample includes a tubular container, a solid rod running though the container, and a stopper and/or valve mounted at the end of the solid rod and manipulated from the exterior of the container at the other end of the container. However, samples taken are often disturbed unsatisfactorily with excessive turbulence caused by the conventional samplers. The excessive turbulence is often caused by restrictions within the tubular container, such as valves, stoppers, flaps, etc., and the design of the plug unit itself. Other devices employ an inlet for receiving the sample that is smaller that the diameter of the tubular container. As a result of these restrictions, the fluid is disturbed and the sample may not be a true sample of the fluid. Thus, what is needed is a sampler that can take a true core sample of the fluid having little if any disturbance caused by excessive turbulence.

SUMMARY

A sampling device for sampling a fluid, especially one having regions of varying densities, is provided. The sampling device can obtain a true core sample of the fluid without having the disturbances caused by excessive turbulence. Because there are no restrictions caused by valves, stoppers, flaps or the like within the retention tube, fluid can flow freely and virtually undisturbed in the retention tube, creating the true core sample of the contents of the body of fluid.

One embodiment of the sampling device includes a hollow retention tube comprising a wall defining an interior space having a first cross-sectional area. The retention tube has an upper end and a lower end that has an opening to receive the core sample of the fluid. The opening preferably has the identical diameter, or cross-sectional area, as the diameter, or cross-sectional area, of the interior space of the retention tube. The retention tube may comprise a material, preferably transparent, such as polypropylene, polycarbonate, LEXAN®, polyvinylchloride (PVC), acrylic, or the like. The retention tube may also come into two or more pieces that can be coupled together with a coupling. The retention tube preferably has a smooth luminal surface and does not have any obstructions within the interior space of the retention tube so that any potential causes for turbulence are removed from within the retention tube.

A control member is also provided. The control member has a proximal end and a distal end, and can be at least partially positioned within the interior space of the retention tube. The proximal and distal ends of the control member can extend through and past the upper and lower ends of the retention tube. The sampling device can also include a plug coupled to the distal end of the control member. The plug can be configured to float in the fluid and/or movable to a position away from the opening of the retention tube to facilitate flow, preferably laminar flow, of the fluid into the tube during insertion of the retention tube into the fluid. The plug can have a portion configured to sealably engage the opening of the retention tube and, after insertion of the retention tube into the fluid, to trap or retain the sample of the fluid within the retention tube. The plug can also have a portion that facilitates laminar flow when being moved from the unengaged position to the engaged position.

In one aspect, the plug can be movable to a position away from the opening of the retention tube, such as adjacent to the retention tube and/or above the lower end of the retention tube. The plug portion can have a second cross-sectional area that is larger than the first cross-sectional area of the interior space of the retention tube. In one example, the plug portion is a first portion, and the plug further includes a top and a second portion coupled between the top and the first portion. The top is configured to self-center into the opening of the retention tube during the withdrawing of the control member and plug. The second portion includes a cylindrical body having a cross-sectional area sized to fit within the opening of the retention tube. In a preferred example, the plug portion can include a flange, and may include a removable gasket to facilitate sealing of the plug. The gasket includes an aperture sized to slidably engage the middle portion of the plug.

The distal end of the control member can be attached to the plug through the bore running through the body of the plug. Preferably, the plug includes a hollow body of a first material, and a filling disposed within the hollow body of a second material that is less dense than the first material. For example, the first material can be PVC and the second material can be a closed-cell foam rubber. In one example, the device includes a cap configured to couple to another tubular member n order to extend the length of the retention tube.

In another aspect, the control member comprises a material, such as nylon, polyester, polyester/nylon combination, polypropylene, or the like. The control member can have an elasticity to stretch beyond the length of the control member momentarily under a jolt to the retention tube. This momentary stretch can allow the plug to temporality become disengage or dislodged from the opening of the retention tube, thereby releasing a portion of the core sample from the retention tube to form a lab sample. In other aspects, the proximal end of the control member can be attached to a handle for manipulating the control member axially in the upward or downward direction. A means for affixing a portion of the control member for maintaining the sealably engaged plug with the opening of the retention tube can also be provided. The means for affixing can be attached to the support jacket and/or the retention tube.

Yet, in another aspect the sampling device includes a support jacket that partially surrounds a portion of the retention tube to provide column strength to the retention tube. The support jacket can frictionally engage with an exterior portion of the retention tube. The support jacket may also have a portion partially surrounding the retention tube to define a window through which the fluid within the retention tube can be observed and/or a portion completely surrounding the retention tube. The exterior surface of the support jacket and/or the retention tube can include markings representing a predetermined scale to indicate the characteristics of the true core sample, such as, but not limited to, a total amount of fluid, and an amount and a number of regions of varying densities.

In another embodiment, a method of obtaining a sample of a body of fluid that may include regions of varying density is also provided. One step can be to provide the sampling device, described above. The sampling device can be lowered into the body of fluid, preferably vertically, while the plug is displaced away from the opening of the retention tube. The plug may float or otherwise be positioned adjacent to the retention tube and/or above the lower end of the retention tube. This can ensure that, when the lower end of the retention tube initially enters and is maintained in the body of fluid, the retention tube can be filled with the sample of the body of fluid without interaction with the plug. Another step can be to apply a withdrawing force or to pull the proximal end of the control member away from the upper end of the retention tube. This motion can permit the plug to sealably engage with the lower end of the retention tube and to retain the sample within the retention tube. The proximal end of the control member can be affixed in order to maintain the seal created by the plug. The sampling device can be lifted out of the body of fluid without disengaging the sealably engaged plug. The true core sample can be removed by fully removing the plug from sealing contact with the retention tube. Another step can be to jolt the retention tube to cause the control member to stretch momentarily to disengage the plug temporarily and to release a portion of the core sample from the retention tube to form a lab sample.

The above, as well as other advantages of the present invention, will become readily apparent to those skilled in the art from the following detailed description of a preferred embodiment when considered in the light of the accompanying drawings.

DESCRIPTION OF PREFERRED EMBODIMENTS

Referring generally to all of the figures, where like reference numerals represent like components, one embodiment of a sampling device 10 is provided to be used to provide samples of contents of a body of fluid 12. The sampling device 10 can be lowered, preferably in a vertical alignment, into the body of fluid 12 and raised to observe the contents. The method of using the sampling device 10 will be described below in further details.

Figure 1:
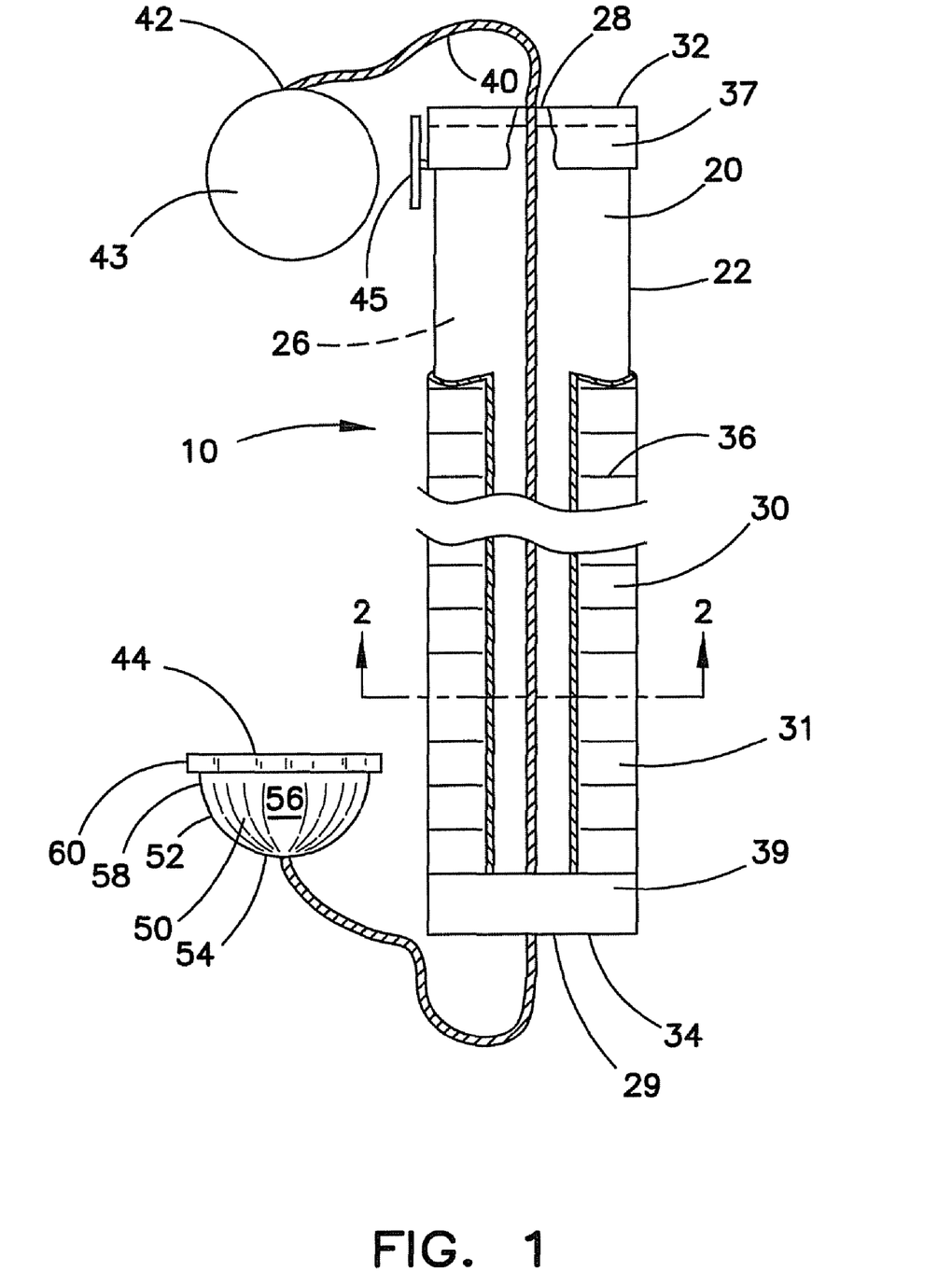
FIG. 1 is an elevation view of one embodiment of a sampling device.
Figure 2:
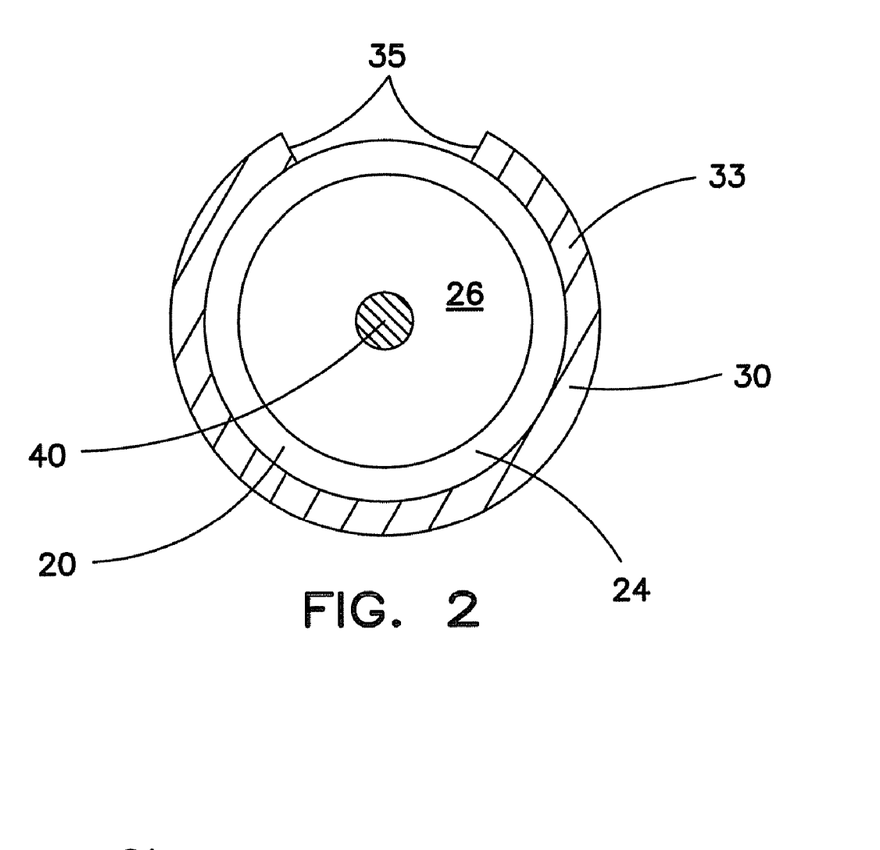
FIG. 2 is a cross-sectional view of the sampling device taken along line 2-2 of FIG. 1.

Referring to FIG. 1, one embodiment of the sampling device 10 includes a retention tube 20. The retention tube 20 provides a general body 22 to retain the sample. Although the body 22 of the retention tube 20 shown in FIG. 1 is cylindrical, the body 22 of the retention tube 20 can be other shapes, including rectangular, oval, or the like. The body 22 of the retention tube 20 has a thin wall 24 that defines an interior space 26 having a predetermined cross-sectional area, as shown in FIG. 2. The wall 24 can be very thin due to an optional structural support of an exterior support jacket 30; for example, the wall thickness can be about 1.3 mm (0.05 inches), although the wall thickness can be more or less depending on the application. Also, the thinness of the wall 24 can permit easier penetration through sludge or other thickened or solidified portion of the sample. One example of the retention tube 20 is a cylindrical tube with the interior space 26 having a diameter of about 4.2 cm (1.65 inches), or the cross-sectional area of about 55 cm$^2$ (8.5 in$^2$). Located at the ends of the retention tube 20 are an upper end 28 and a lower end 29. The lower end 29 is the fluid receiving end, and is adapted to be inserted into the body of fluid 12. It is through the lower end 29 where a core sample of the fluid is received. The opening through the lower end 29 preferably has the identical diameter as the diameter of the interior space 26 of the retention tube. This permits the sample to be taken with minimal disturbance or turbulence that is caused in the devices with smaller diameters, transitions, and/or flanges at the opening. In addition, devices with these smaller diameters at the opening form additional surface at the lower end which pushes sludge away from the opening. The upper end 28 of the retention tube 20 is held above the body of fluid 12 and can have an opening equivalent or substantially similar to the lower end 29.

The wall 24 of the retention tube 20 can be made of plastic material that is inert to most chemicals and rigidly strong and unbreakable, such as polypropylene, polycarbonate, LEXAN®, polyvinylchloride (PVC), acrylic or the like. Preferably, the material of the retention tube 20 is transparent to allow the user to observe and analyze the contents more easily. The wall material, wall thickness and the cross-sectional area of the retention tube 20 can be selected in order for the retention tube 20 to obtain a sampling capacity of about 1.0 Liter per meter (10 ounces per foot) or more without the support jacket to about 1.4 Liters per meter (14 ounces per foot) or more with the support jacket. Preferably, the inside surface of the wall 24 of the retention tube 20 has a smooth surface finish to provide effective sealing and to facilitate laminar flow of the fluid through the lumen 26 of the retention tube 20 during insertion of the retention tube 20 into the body of fluid 12.

The support jacket 30 can be provided to provide column strength to the retention tube 20. The support jacket 30 can surround a portion of the retention tube 20, or the entire the retention tube 20. The support jacket 30 can be friction fitted around the retention tube 20, where the support jacket 30 can be removed for cleaning. Optionally, the support jacket 30 can be bonded with the retention tube 20 with adhesives. FIG. 2 is a cross-sectional view taken a line 2-2 of FIG. 1 of the sampling device 10, illustrating the proximity of the support jacket 30 and the retention tube 20. The support jacket 30 preferably has a length between an upper end 32 and a lower end 34 that is substantially similar to the length of the retention tube 20. The support jacket 30 provides a general body 31 that can be similarly shaped as the retention tube 20. The body 31 of the support jacket 30 shown in FIG. 1 is cylindrical having a wall 33 with a thickness suitable to support the retention tube 20. The support jacket 30 can be molded or extruded as a cylindrical unit with a portion removed to form a window 35 for observation of the contents of the fluid sample within the retention tube 20.

The support jacket 30 can be made of the same material, but it is desirable that the support jacket be made of less expensive material because of the supporting function. Examples of the material of the support jacket 30 can be polycarbonate, PVC, acrylonitrile butadiene styrene (ABS), polypropylene, or other suitable materials with the desired properties. In some embodiments, the material of the support jacket 30 can be an opaque material so long as an adequate space, separation, or the window 35 is provided. At least one portion of the support jacket 30 can completely surround a portion of the retention tube 20 to provide extra support at that specific region of the retention tube 20. For example, FIG. 1 illustrates end caps 37, 39 at the ends 28, 29 of the retention tube 20. The end caps 37, 39 are preferably made of the same material as the support jacket 30, although the end caps 37, 39 can be made of a different material having properties specific for the application. Portions of the end cap 37 and the support jacket 30 are cut away to illustrate the retention tube 20. The upper end cap 37 can be positioned around the upper end of the retention such that the upper end cap 37 extends past the upper end. The amount of extension and cross-section and/or diameter of the upper end cap 37 should be sufficient in order to receive another tube, as described below.

Markings 36 indicating a scale can be provided on the exterior surface of the support jacket 30, as shown in FIG. 1. Optionally, the markings 36 can be provided on the retention tube 20. The markings 36 can be at any desired increment. In one example, the markings 36 can be marked for every 0.1 meter and numbered for every 0.5 meter (or marked for every 6 inches and numbered for every foot). The markings 36 can represent a predetermined scale to indicate to indicate characteristics of the fluid, such as the depth of the body of fluid 12, the total amount of the core sample of the fluid, and/or the amount and the number of regions of the fluid with varying densities.

Extending at least partially through the interior space 26 of the retention tube 20 is a control member 40 having cross-sectional area substantially smaller than that of the interior space 26 of the retention tube 20, as shown in FIG. 2. The control member 40 can be rope, cable, cord, or the like. The material of the control member 40 should be capable of maintaining an original length with the weight of the contents of the fluid inside the retention tube 20. In other embodiments, the material of the control member 40 should also be adapted to allow for a momentary deformation of about 0.5% to about 10%, more preferably, about 1% to about 5%, under about 10-50 pounds (force), under a jolt or quick, vertical force to the retention tube 20. After the jolt, the control member 40 can be capable of returning to the original length. In other words, with the weight of the contents inside the retention tube 20, the control member 40 can have an elasticity to stretch beyond the original length of the control member 40 momentarily under a jolt to the retention tube 20 to allow at least a portion of the contents to be exit from the retention tube 20. The material of the control member 40 should also not rot or mildew. The control member 40 is preferably a rope comprising nylon, polyester, polyester/nylon combination, or other materials stranded, braided or weaved, known by one skilled in the art that exhibit such characteristics, such as a double braided polypropylene marine rope.

The control member 40 has a proximal end 42 and a distal end 44, and a length that can be substantially longer than the length of the retention tube 20. The length of the control member 40 can depend on the length of the retention tube 20 and the depth of the body of fluid 12, especially when the plug 50 is capable of floating to the surface of the body of fluid 12 which adds considerable length to the control member. The proximal end 42 of the control member 40 can be attached to a handle 43 and used to manipulate the control member 40 axially in the upward or downward direction. FIG. 1 illustrates the handle 43 as a spherical handle made of closed-cell foam rubber, though the handle can be made of other materials, such as plastics, other spongy foams, wood, or the like. The cross-sectional area of the handle can be greater than the retention tube 20 to prevent the handle from slipping through the lower end 29 of the retention tube 20. The handle 43 can include other shapes, such as a cylindrical handle or a handle having an aperture configured for a hand to fit therethrough.

Figure 4:
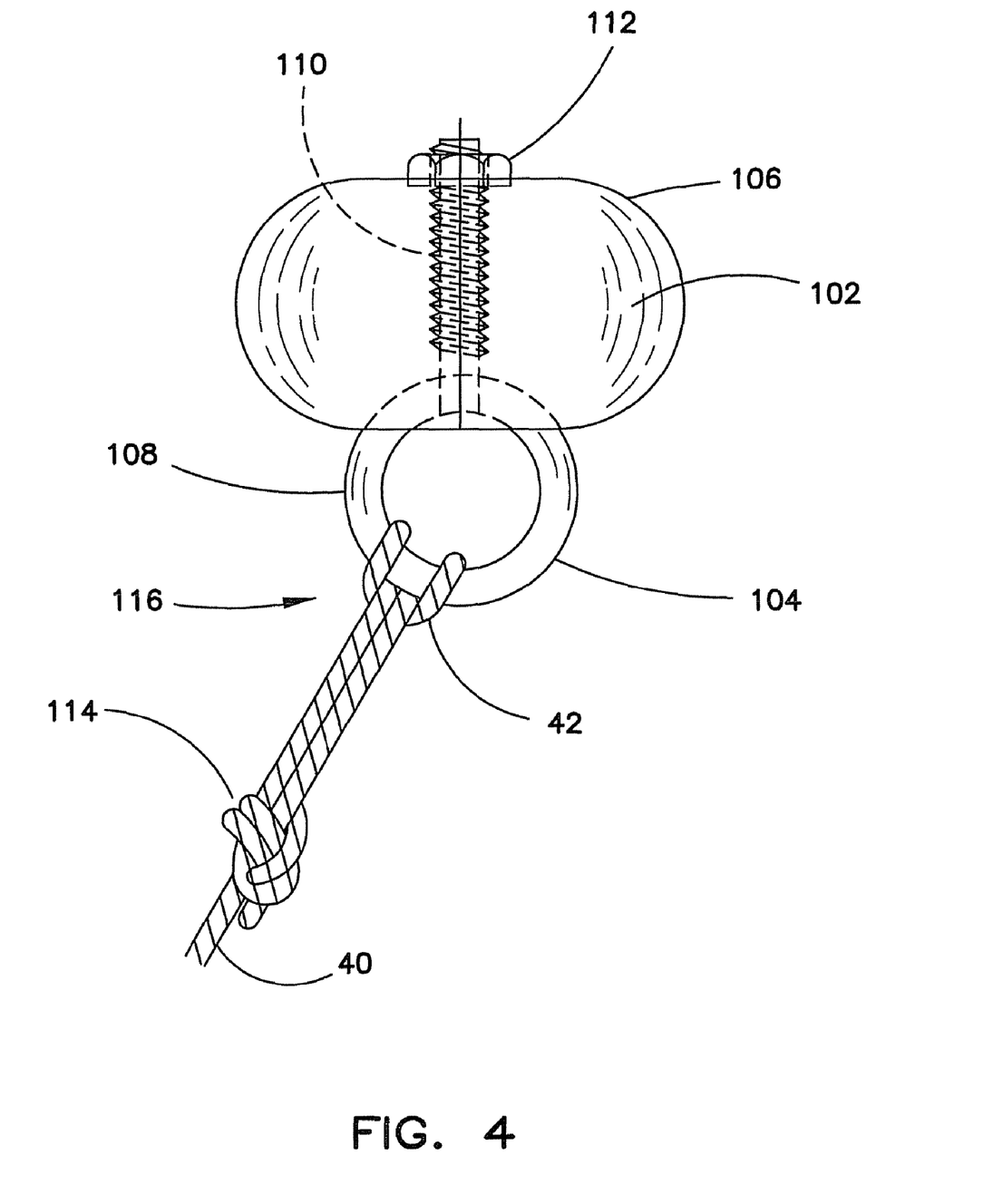
FIG. 4 is a side view of a handle of one embodiment of a sampling device.

One exemplary handle is illustrated in FIG. 4. The handle 102 is a solid, spongy cellular material shaped oblong with an eyelet bolt 104, preferably stainless steel, extending through a bore 106 in the middle of the handle 102. The eyelet bolt 104 includes a ring structure 108 attached to threaded shaft 110. A nut 112 is threadably engaged with the threaded shaft 110 for fixedly attaching the eyelet bolt 104 to the handle 102. The cross-sectional area of the handle 102 can be greater than the cross-sectional area of the retention tube 20. The ring structure 108 is used to attach to the proximal end 42 of the control member 40 via a knot, loop, adhesive, welding, or the like.

Preferably, the control member 40 can be easily removed and reattached for situations requiring longer rope, extensions or different handle configurations. Though several different kinds of knot or loops can be used, one preferred loop is the figure eight loop 114 shown in FIG. 4. After knotted, the loop 116 can be inserted through the ring structure 108 and expanded to slide over the handle 102 in order for the control member loop 116 to couple to the ring structure 108.

The handle 43 can be adapted to pull or withdraw the proximal end 42 of the control member 40 with a force sufficient to pull a plug 50 against the lower end 29 of the retention tube 20. Once the plug 50 is sealably engage and seated, the proximal end 42 and/or proximal portion of the control member 40 is affixed, clamped, or otherwise manipulated to maintain the sealing function of the plug 50 before and after removing the retention tube 20 from the body of fluid 12.

One nonlimiting example of how the control member 40 is affixed is by a cleat hitch 45, as shown in FIG. 1. The cleat hitch 45 includes a main body with a pair of cleat horns projecting therefrom. The main body of the cleat hitch 45 also includes a mounting surface that can be attached to the exterior surface of the retention tube 20 or the support jacket 30, or optionally the upper end cap 37. Preferably, the cleat hitch 45 can be generally oriented to have the cleat horns in alignment with the retention tube 20 or the support jacket 30. In order to secure the control member 40 to the cleat hitch 45, the control member 40 is wrapped around the cleat horn furthest from where the control member 40 comes from, similar to tying a boat to a dock cleat. One wrap of the control member 40 can be taken around the main body of the cleat hitch 45 and can start a figure eight across the top of the opposite cleat horn. Finish with a half hitch turned under so that the control member 40 is going away from the cleat hitch 45 in the opposite direction from where the control member 40 came from. It is appreciated that one skilled in the art can use other devices and methods can be used to affix the proximal portion of the control member 40, such as other types of knots, clamps, or the like.

Figure 3A:
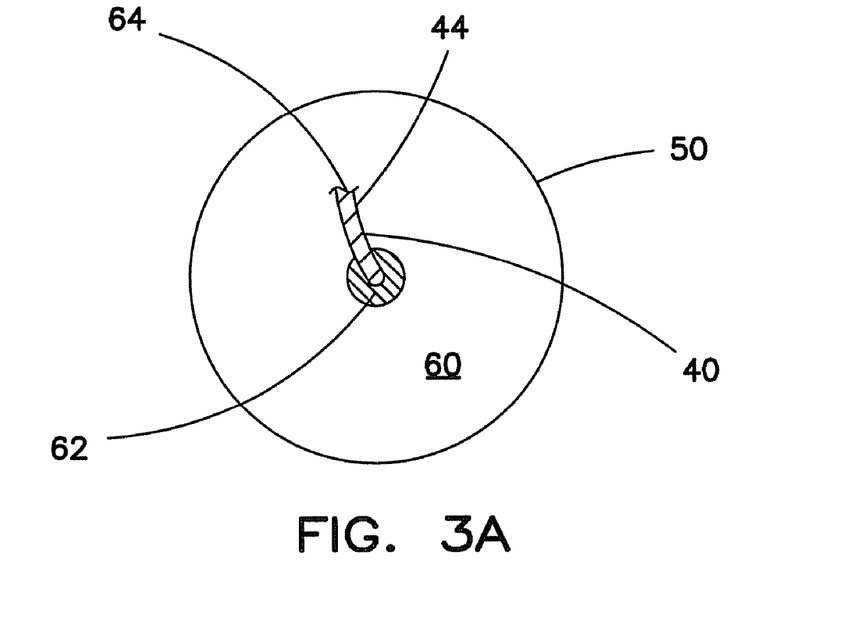
FIG. 3A is a bottom view of one embodiment of a plug of a sampling device.
Figure 3B:
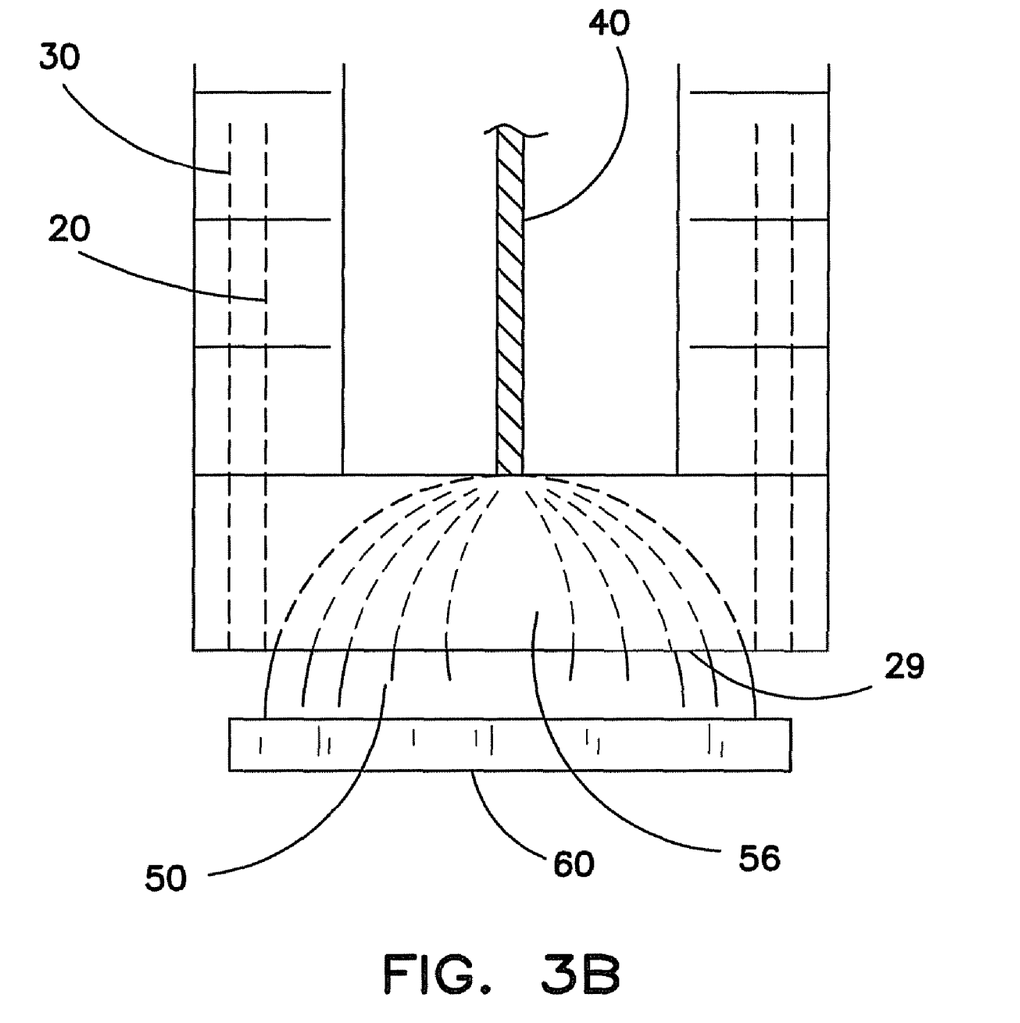
FIG. 3B is a cross-sectional view of the lower end of an engaged plug of the sampling device of FIG. 1.

The plug 50 is attached at the distal end 44 of the control member 40. Referring to FIG. 1 and FIGS. 3A-3B, the plug 50 includes a plug body 52 that is configured to be moved through the fluid to a position adjacent to the retention tube 20 that can also facilitate laminar flow of the fluid into the retention tube 20 during insertion of the retention tube 20 into the body of fluid 12. In order for the plug 50 to not further disturb the fluid, the plug 50 can also be configured to have a suitable buoyancy to float up at least along the side the retention tube 20 well clear of where the fluid enters the retention tube 20.

The plug 50 can have a first portion 54 with a surface 56 having a cross-sectional area that is larger than the cross-sectional area of the interior space 26 of the retention tube 20. In general, the overall shape of the first portion 54 of the plug 50 has a periphery 58 to match the general shape of the retention tube 20. Preferably, a region of the first portion 54 is curved and/or a tapered surface configured to allow the plug to self-center upon insertion and/or to facilitate laminar flow from non-engagement to insertion. A spherical surface 56 is shown and configured to extend inside of the retention tube 20, as shown in FIG. 3B. A portion of the first portion 54 of the plug 50 can sealably engage and seat the lower end 29 of the retention tube 20 to physically block the opening at the lower end 29 of the retention tube 20. After insertion of the retention tube 20 into the body of fluid 12, the plug 50 can be moved into position to sealably engage the lower end 29 of the retention tube 20 to trap the core sample of the fluid within the retention tube 20. In one example, the first portion 54 of the plug 50 has a hemispherical-like or dome-like shape, as shown in the Figures.

The plug 50 can also include a second portion 60 to which attaches to the distal end 44 of the control member 40 to prevent the plug 50 from being pulled in too far within the retention tube 20. The second portion 60 can be affixed to the first portion 54 through thermal bonding, bonding with an adhesive, and/or sealed with the first portion 54 of the plug 50 to form the plug body 52. The bonding should be able to withstand the applicable fluid environment and the pulling force of the user when sealing the lower end 29 of the retention tube 20. In one example, the second portion 60 can have a cross-sectional area that is at least larger than the cross-sectional area of the interior space 26 of the retention tube 20. Preferably, the second portion 60 has a cross-sectional area that is larger than the cross-sectional area of the first portion 54.

Referring to FIG. 3A, the distal end 44 of the control member 40 attaches to the plug 50. Preferably, the plug 50 includes a longitudinal bore 62 through the center of at least one of the first portion 54 and the second portion 60. In this example, the distal end 44 of the control member 40 attaches to the plug 50 by running through the bore 62 of the plug 50 and attaching at an attachment point 64 proximate about the center of the bore 62 at second portion 60, as shown in FIG. 3A. The distal end of the control member can wrap around the attachment point and attach to another portion of the control member 40 with the application of an adhesive. One example is to attach the distal end 44 of the control member 40 to the plug 50 is for the distal end 44 to threadably engage with a bore 62 that is tapped. In another example, the distal end 44 of the control member 40 is adhesively bonded with epoxy or other adhesives and/or tied to the plug 50, and then vacuum formed or injection molded to form an integral unit.

The first portion 54 and/or second portion 60 of the plug 50 can be molded from a compliant material, such as polyvinyl chloride (PVC), polycarbonate, high density polyethylene (HDPE), ABS, polypropylene, or the like. Preferably, the plug body 52 is a closed-cell foam rubber with a thin shell of plastic that increases the buoyancy. The compliant material can possess sufficient flexibility to create a tight seal, and a sufficient density to promote floatability as discussed herein. It is preferable that the means 43 for manipulating and the plug 50 are manufactured similarly with materials having similar properties.

Figure 5A:
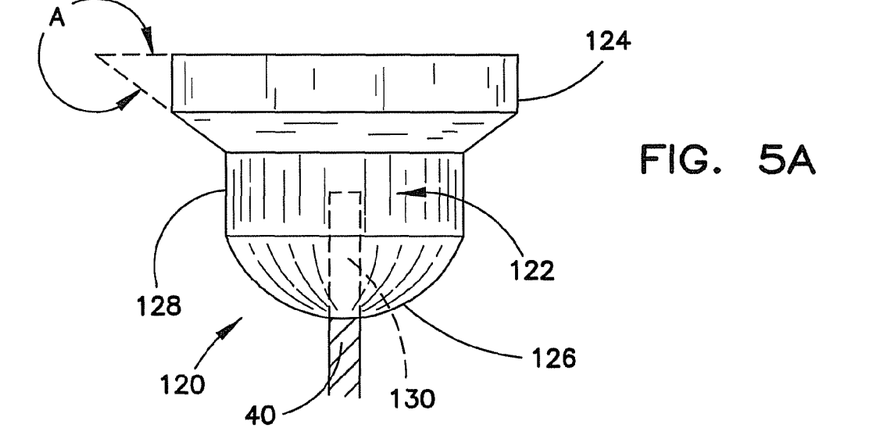
FIG. 5A is a side view of one embodiment of a plug.
Figure 5B:
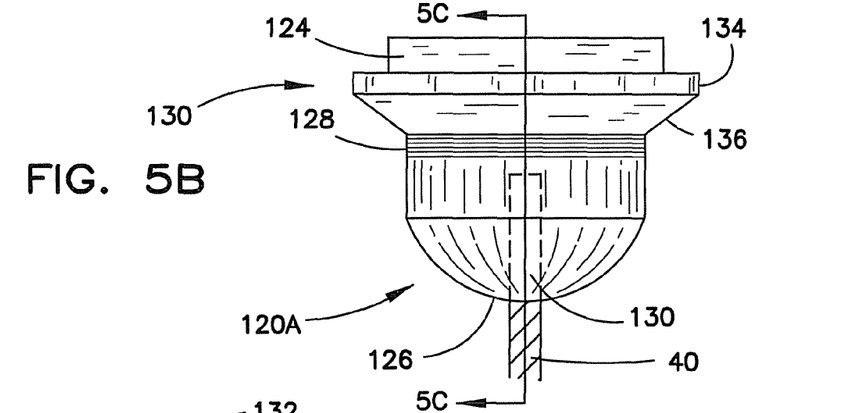
FIG. 5B is a side view of another embodiment of a plug.
Figure 5C:
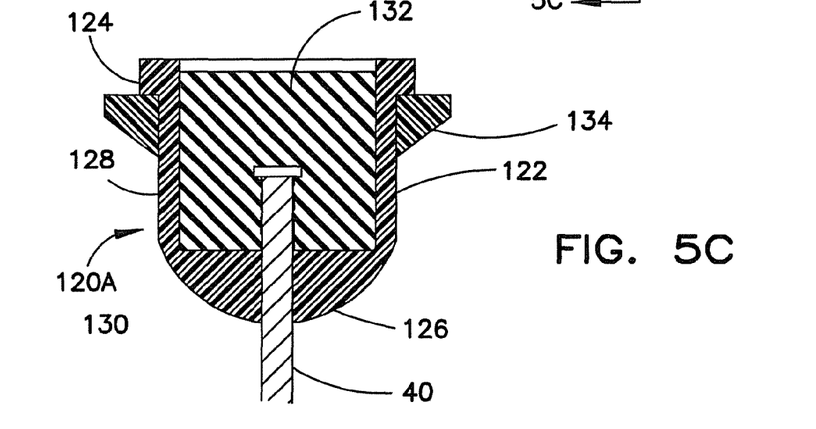
FIG. 5C is a cross-sectional view taken along line 5C-5C of FIG. 5B.

An exemplary plug is depicted in FIGS. 5A and 5B. The plug 120 includes a body 122 having a flange 124, a tapered or rounded cap 126 and a cylindrical middle section 128 coupled therebetween. The body 122 of the plug may also be hollow containing a bore 130 in the middle for receiving a material 132 configured to impart better floatability to the plug. For example, a closed cell rubber foam may be sized to insert within the bore, such as shown in FIG. 5C. The floatable material 132 is preferably attached within the bore 130 with an adhesive. The plug 120 can be made of one of the several materials described above, and molded or machined to shape.

In FIG. 5A, the flange 124 has a cross-sectional area larger that the cross-sectional area of the interior space 26 of the retention tube 20. The flange 124 may be normal to the face of the middle section, having an angle of about 90°. Preferably, the angle A of the flange is sized to seal against the opening of the retention tube and sized to deflect the fluid sample away so that is does not splash toward the operator. The angle can be about 15-75°, and preferably about 60°. The middle section 128 has a cross-sectional area sized to fit within the opening through the lower end 29. Preferably, the cross-sectional area is sized provide a slidable fit within the opening. The length of penetration of the middle section 128 can be between 30-50% of the diameter of the middle section; for example, for a 1.25-inch diameter, the length can be about 0.5 inches. The tapered cap 126 includes the bore 130 for receiving the control member. The tapered cap 126 can have a curvature, such as hemispherical-like or dome like, as shown in the Figures, or be tapered at an angle of about 30-60°. The curvature or tapering permits the plug to self-center when being pulled into contact with the opening, and/or to deflect the fluid sample away so that is does not splash toward the operator. The control member can be attached to the plug 120 through the bore 130 with an adhesive and/or knot.

In a preferred embodiment shown in FIG. 5B, the body 122 of the plug 120A has a 90° flange 124 and further includes a tapered gasket 134. The gasket 134 slidably attaches to the middle section 128 of the plug 120A. The middle section 128 may also be grooved such that the sliding of the gasket 128 can be more easily controlled. The gasket 134 has outside diameter sized to be greater than the diameter of the interior space 26 and an inside diameter slightly larger than the diameter of the middle section 128. The gasket 134 can have a portion 136 that is tapered from the outside diameter to the inside diameter of the gasket. Preferably, the angle of the taper is sized to seal against the opening of the lower end 29 of the retention tube 20 and sized to deflect the fluid sample away so that is does not splash toward the operator. The angle can be about 15-75°, and preferably about 60°. The gasket 134 is preferably made of a softer material (about 70-90 durometer (Shore) A), such as polyethylene, than the plug body (for example PVC with a hardness of about 70-90 durometer (Shore) D) for facilitating a better seal against the opening at the lower end. Too soft of a material (less than about 70 durometer (Shore) A), such as rubber, permits the gasket to "stick" against the opening during an attempt to remove the plug from within the opening at the lower end more difficult. The gasket 134 can be easily replaced without having to replace the entire plug body 122, and can be used to optimize the seal between the opening at the lower end 29 and the plug 120A since the gasket 134 can made of different shapes and materials than that of the plug body 122. The control member 40 can be attached to the plug 120A through the bore 130 with an adhesive and/or knot.

To sample fluid from a body of fluid 12, the retention tube 20 and/or the support jacket 30 can be extended to any length. Preferably, the retention tube 20 and/or the support jacket 30 are manufactured in at about 2.4-meter (8-foot) lengths to fit within the bed of a full size pickup truck or 1.2-meter (4-foot) lengths to fit within a smaller vehicle to facilitate shipping and transporting of the sampling device 10. 1.2-meter (4-foot) extension sections can be removably attached to each other to increase the total length of the sampling device 10 to about 2.4 meters (8 feet), 3.6 meters (12 feet), 4.8 meters (16 feet) or more, although the extension sections of the retention tube 20 and/or support jacket 30 can be manufactured in any length. The extension sections can be removably attached by any slip fit or threaded male/female fittings known by one skilled in the art. The extensions may be coupled to the retention tube by use of a coupling which provides a tight friction fit. For example, the coupling can be sized and configured sufficiently to receive a first and a second portion of the retention tube and/or a second retention tube or another tubular member. The coupling is preferably a slip joint which typically has a slightly tapered surface such that the diameter of the lumen gradually reduces for better friction fitting. Threads are not needed at this coupling since after the sample is taken the plug is sealed and the second handle is tied together compressing the pieces together. Threads in many instances are undesirable because of the potential of dirt clogging the threads and/or cross-threading.

Figure 6:
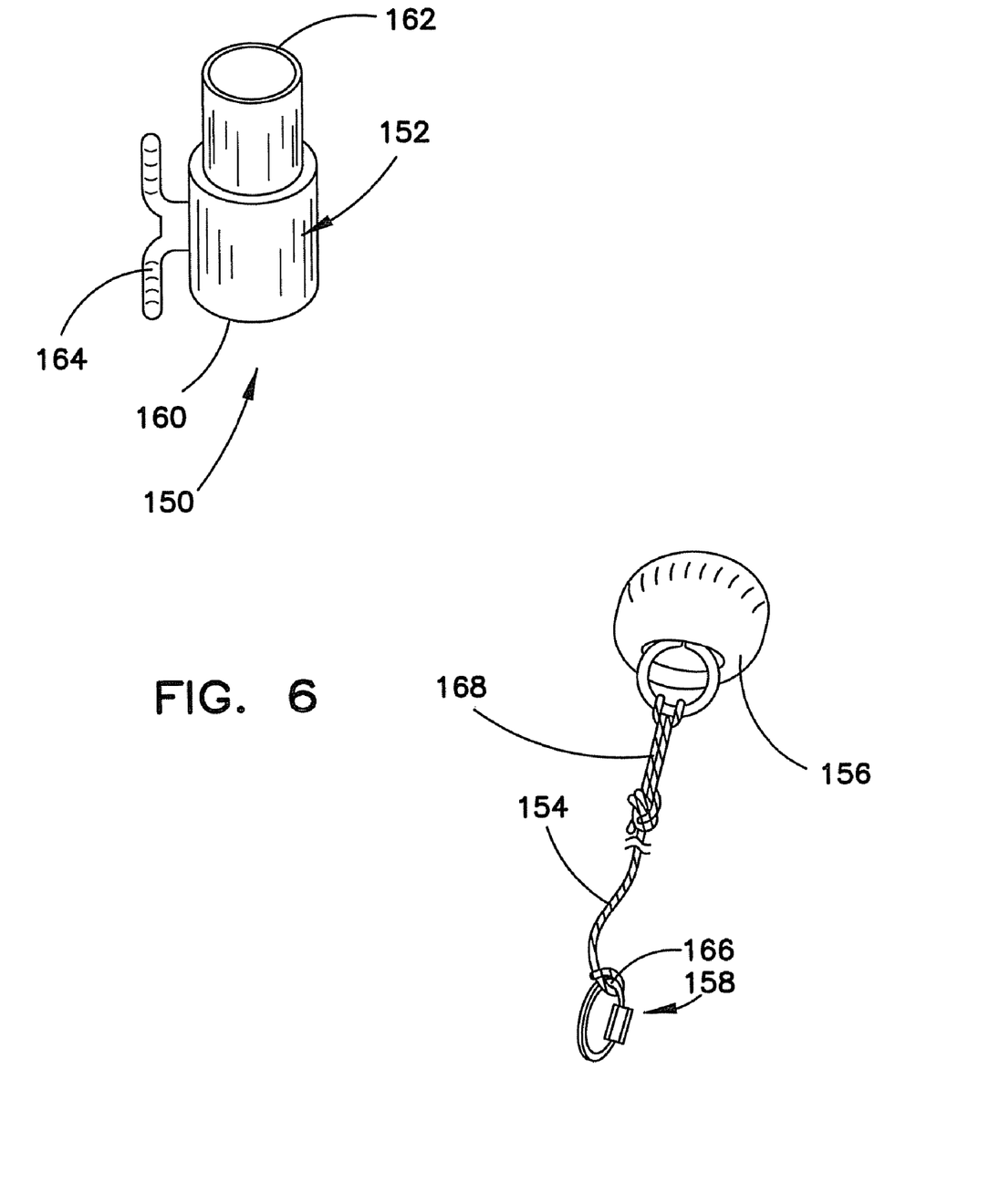
FIG. 6 depicts a kit used with a sampling device.

With reference to FIG. 6, a kit 150 can be provided to extend the length of the retention tube 20. The kit 150 can include a coupling 152, such as described above, a second control member 154 with or without a second handle 156 (shown with a second handle), and a quick coupling 158. The coupling 152 includes a first end 160 sized to receive the upper end of the extension tube (not shown), a second retention tube or another tubular member such as PVC pipe, and a second end 162 for engaging the handle. A cleat hitch 164 can also be attached to the coupling 152 and arranged as described above. The coupling 152 is attached to the upper end of the extension tube, either through a tight slip friction fit or threaded connection. The original handle can be removed from attachment to the original control member, and reattached to the second control member 154 if a second handle is not provided. Once detached from the original control member, the loop end 166, opposite the handle end 168, of the second control member 154 can be fed through the tubular member. The handle can be attached to the handle end 168 as described above, if not already attached, and the loop end of the original control member can then be coupled to the second control member 154 via the quick coupling 158. After coupling, the original retention tube can be coupled to the tubular member by inserting the lower end of the tubular member into the upper end cap of the retention tube. This coupling is preferably a tight friction fit.

Figure 7A:
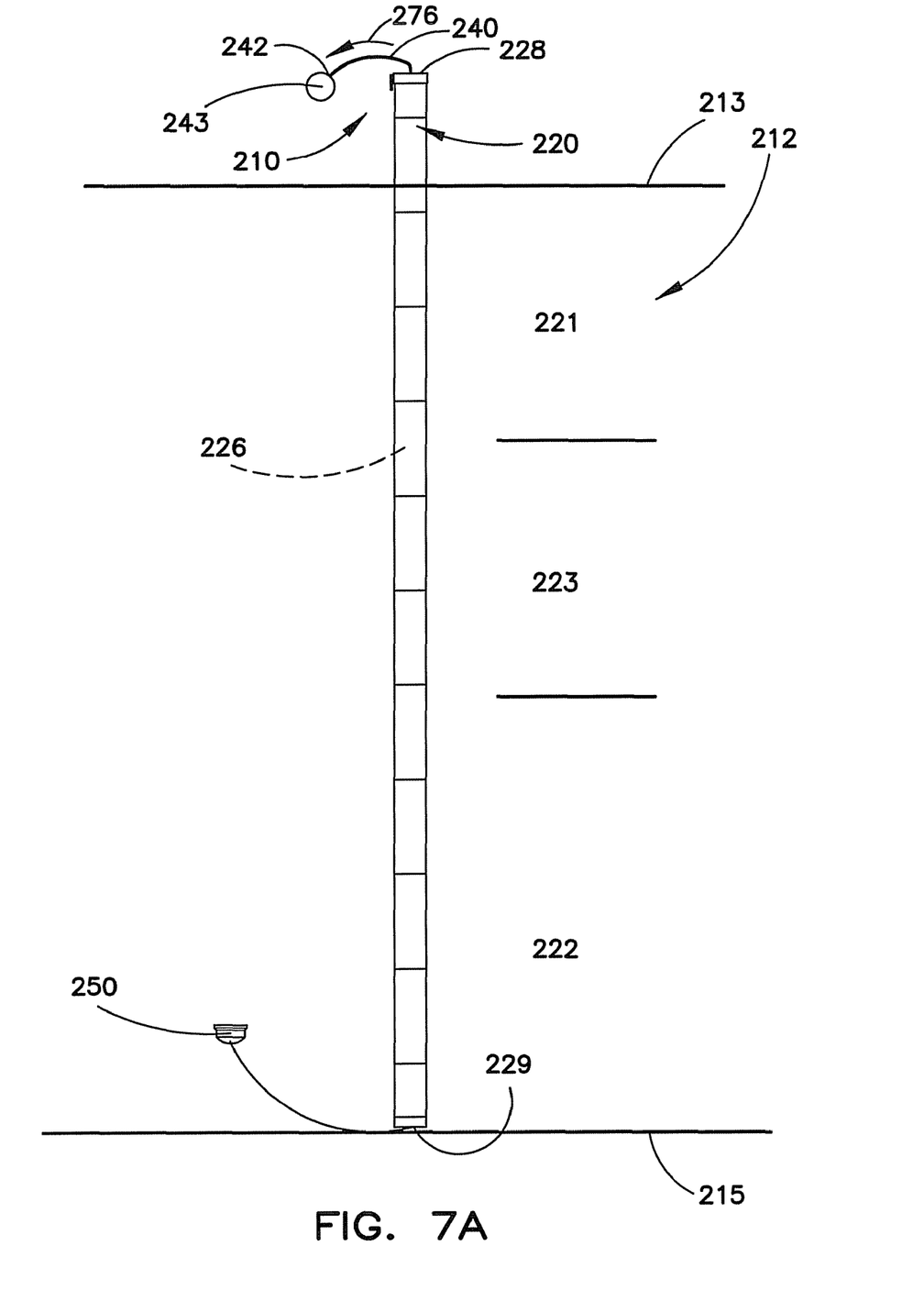
FIG. 7A is an elevation view of a sampling device surrounded by a body of fluid, with the sampling device containing a sample of the body of fluid.

Referring now to the operation of the sampling device 10 by an operator, the sampling device, referred to as 210, is used to provide samples of contents of the body of fluid 212, as shown in FIG. 7A. The body of fluid 212 could be found in a drum or like receptacle, a tank such as a wastewater treatment tank, or other body of fluid such as a pond, lake, or the like. The body of fluid 212 includes an upper surface 213 and a lower surface 215 and a may include regions of uniform or varying densities therebetween. For example, the fluid 212 could be all liquid, or optionally, a liquid 221 disposed above a solid layer of caked sludge 222 and/or semi-solid layer 223 of caked sludge at the bottom thereof. A sample can have a wide range of settled solids. Further, the fluid 212 may have a solidified top layer or scum. Regardless of the exact make up of the fluid 212, the sampling device 210 can provide an accurate, reliable sample of the contents of the body of fluid 212, including a core sample reflecting the various strata, if any, of the fluid forming the contents.

Figure 7B:
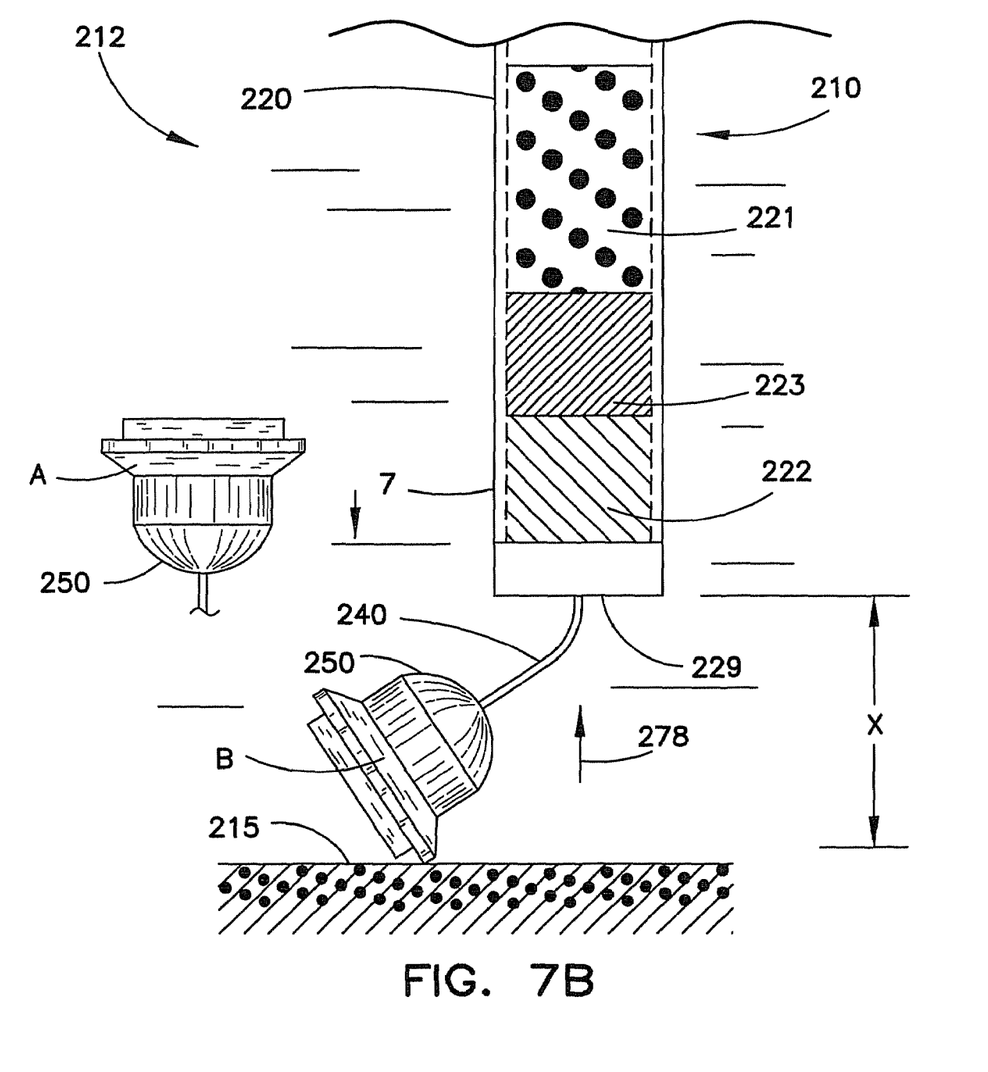
FIG. 7B depicts a detailed view of a distal portion of the sampling device in FIG. 7A.

Generally referring to all the Figures, and specifically FIG. 7A, when the user is proximate the body of fluid 212, the control member 240 can be relaxed to disengage the plug 250 from a closed or sealed position against the lower end 229 of the retention tube 220 to open the opening at the lower end 229 thereof. The user can orient the sampling device 210 generally in a vertical orientation, with the plug 250 and the lower end 229 of the retention tube 220 at the lowermost point. The sampling device 210 can be lowered into the body of fluid 212 to a desired distance while the plug 250 is displaced to a location adjacent the retention tube 220. This occurs when the lower end 229 of the retention tube 220 initially enters the body of fluid 212 in order to allow the retention tube 220 to be filled with a core sample of the body of fluid 212 without interaction with the plug 250. The plug 250 may float at the upper surface 213 of the body of fluid 212, or somewhere in between the upper and lower surfaces 213, 215 depending on the density of the fluid 212 and/or plug and the length and slackness in the control member 240. While being lowered, air is permitted to escape from the upper end 228 of the retention tube 220. The sampling device 210 may be lowered at a suitable rate to reduce the risk of creating excessive turbulence of the fluid 212 entering or surrounding the sampling device 210 and to obtain a true core sample of the body of fluid 212. The fluid 212 may continue to flow freely and virtually undisturbed into the retention tube 220, creating the true core sample of the contents of the body of fluid 212, because there are no restrictions within the interior space 226 of the retention tube 220, such as valves, stoppers, flaps or the like. FIG. 7A illustrates the lower end 229 cutting right through the sludge 222 until hitting the lower surface 215. More specifically, to get a sludge sample, the sampling device 210 can be pushed down into the sludge 222, with possible other layers of liquid and solids as described above. The thin walls of the retention tube 220 and/or the support jacket can cut through most types of sludge. In order to seat the plug 250 into the lower end 229, the retention tube 220 can be lifted from the floor 215 or bottom of the body of fluid by a specified distance, shown as X, (e.g., about 1 inch or more) suitable to permit the plug to be seated, as shown in FIG. 7B.

Figure 7C:
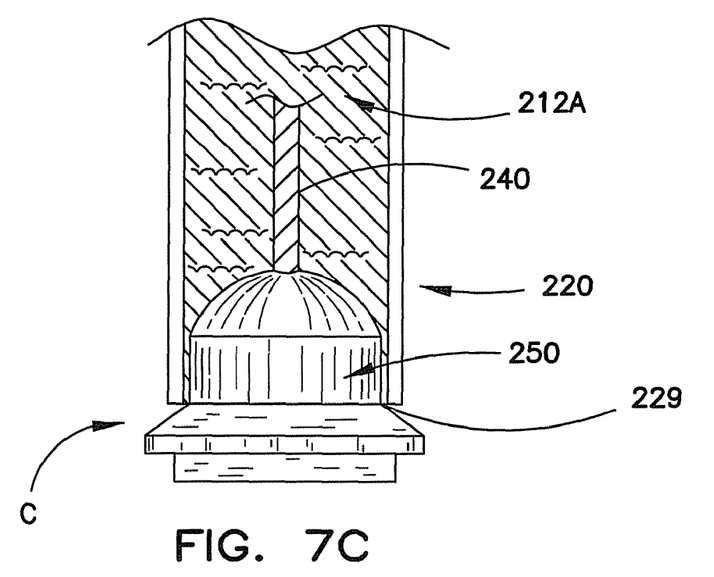
FIG. 7C is a detailed view of the end of the sampling device of FIG. 7A, depicting the plug in a closed position.

After a satisfactory sample of the contents of the body of fluid 212 is taken, the user can apply a withdrawing force, represented by arrow 276, to the handle 243, as shown in FIG. 7A. The proximal end 242 of the control member 240 can be manipulated to cause the plug 250 to move from the position A to another position B, as shown in FIG. 7B, which depicts the distal portion of the retention tube within the body of fluid. The force 276 exerted by the user can urge the control member 240 and the plug 250 to move at a suitable rate to minimize disturbance of the sample within the retention tube 220 and the surrounding fluid 212. For example, the rate of movement toward the retention tube 220, represented by arrow 278, can be about 0.3 meter per second (1 foot per second). The withdrawing force 276 is continually applied until the plug 250 is sealably engaged and seated within the lower end 229 of the retention tube 220 to a position C, as shown in FIG. 7C. FIG. 7C also illustrates the wall of the retention tube 220 in relation to the position of the plug 250 when seated within the lower end 229. Once in the closed position, the plug 250 can trap the core sample 212A of the fluid 212 within the retention tube 220. The proximal end 242 of the control member 240 can then be affixed or tied, as described herein, to maintain a sufficient force to the plug 250 for maintaining the seal between the plug 250 and the retention tube 220.

The sampling device 210 can be lifted by the user at a suitable rate to minimize disturbance of the sample 212A within the retention tube 220 and the surrounding fluid 212. For example, the sampling device 210 can be lifted at a rate of about 0.6 meter per second (2 feet per second). The user should lift the sampling device 210 in a vertical fashion slowly from the body of fluid 212 without disengaging the sealably engaged plug 250. Fluid left on the external surface of the sampling device 210 can then be allowed to drip off into the body of fluid 212 or removed by an absorbent material. After the analysis of the sample 212A, the sample 212A can be removed and the retention tube 220 emptied by disengaging the control member 240 to allow the plug 250 to disengage from the retention tube 220. The sample 212A can be emptied into a collection container or back into the body of fluid 212. Thereafter, the sampling device 210 can be rinsed with water.

Figure 7D:
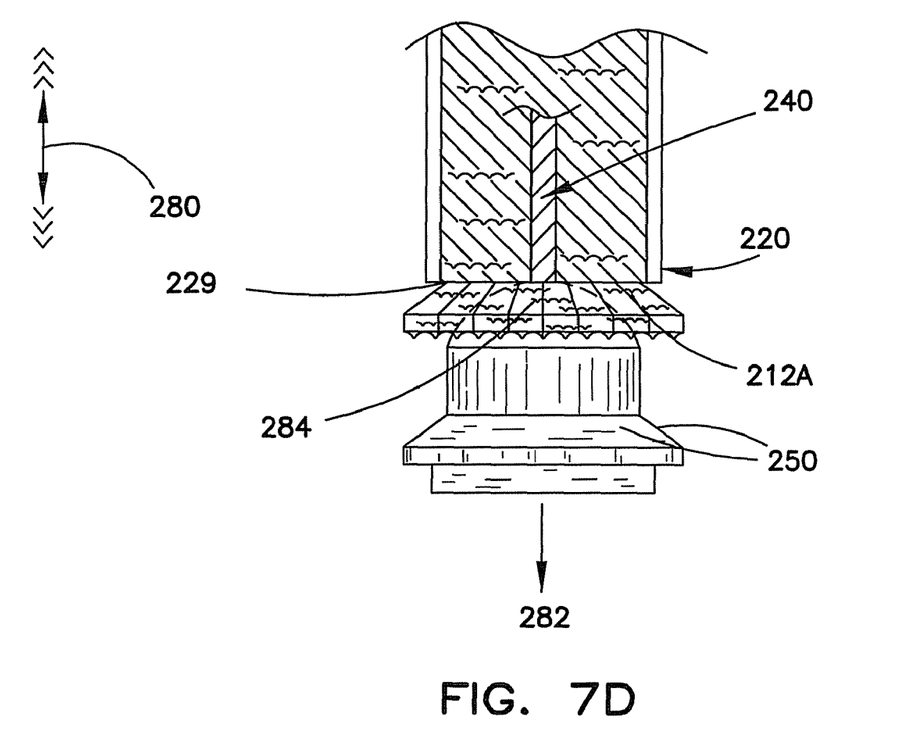
FIG. 7D is a detailed view of the end of the sampling device of FIG. 7A being jolted to release at least a portion of the sample.

In another example shown in FIG. 7D, the user can jolt with a sufficient force and motion, represented by arrow 280, the sampling device 210, while the plug 250 is sealably engaged and seated within the retention tube 220. This can cause the control member 240 to stretch momentarily away from the retention tube 220, represented by arrow 282. This temporarily disengages the plug 250 from retention tube 220 so that a small sample and/or a lowermost portion of the core sample is released out of the lower end 229 of the retention tube 220, represented by arrows 284. As shown, upon release from the end, the sample deflects downward and radially outward from the tapered or rounded cap of the plug. This feature is particularly useful when a small sample is desired, such as a lab sample, instead of the entire contents within the retention tube 220. The lab sample can be analyzed and finding recorded before completely releasing the fluid from the retention tube 220.

The sampling device, of any of the embodiments described above, can be easily cleaned because the device does not have to disassembled. Further, with no restrictions in the retention tube, the retention tube can be easily cleaned using a tube brush or squeegee device. The support jacket and/or the control member can be removed from the retention tube to facilitate the cleaning of the individual components. Cleaning should be after every use in order to avoid the possibility of contaminated subsequent samples.

In accordance with the provisions of the patent statutes, the present invention has been described in what is considered to represent its preferred embodiment. However, it should be noted that the invention can be practiced otherwise than as specifically illustrated and described.

The invention claimed is:

1. A sampling device for sampling a fluid, the device comprising:
   a retention tube comprising a wall defining an interior space with a first cross-sectional area, the retention tube having an upper end and a lower end and an opening at the lower end to receive a sample of said fluid;
   a control member having a proximal end and a distal end, the control member being at least partially positioned within the interior space of the retention tube, the proximal and distal ends of the control member extending through and past the respective upper and lower ends of the retention tube; and
   a plug coupled to the distal end of the control member, the plug being movable to a position adjacent to the retention tube and above the lower end of the retention tube to facilitate flow of said fluid into the retention tube during insertion of the retention tube into said fluid, the plug comprising a portion having a second cross-sectional area larger than the first cross-sectional area of the interior space of the retention tube, the plug being configured to sealably engage the opening of the retention tube so that a sample of said fluid is retained within the interior space of the retention tube,
   wherein the plug comprises a top, a flange, and a middle portion coupled between the top and the flange, the top being configured to self-center into the opening of the retention tube, the middle portion having a cylindrical body having a cross-sectional area sized to fit within the opening of the retention tube, the plug comprising a removable gasket having an aperture sized to slidably engage the middle portion of the plug, the removable gasket comprising a material having a lower durometer than a material of the top, the flange, and the middle portion of the plug.

2. The device of claim 1, wherein the retention tube comprises a material configured to permit visual inspection of said sample within the retention tube.

3. The device of claim 1, wherein the retention tube further comprises a cap disposed at the upper end thereof, the cap having a first end configured to receive the upper end of the retention tube and a second end configured to receive an end of a tubular member.

4. The device of claim 1, wherein the opening and the interior space of the retention tube each have substantially identical cross-sectional areas.

5. The device of claim 1, wherein the interior space of the retention tube does not have any obstructions between the upper and lower ends.

6. The device of claim 1, wherein the control member comprises a material selected from the group consisting of nylon, polyester, polyester/nylon combination, and polypropylene.

7. The device of claim 6, wherein the control member comprises an elasticity adapted to stretch momentarily under a jolt to the retention tube.

8. The device of claim 1 further comprising a handle removably coupled to the proximal end of the control member, the handle being configured to manipulate the control member axially along the interior surface of the retention tube.

9. The device of claim 8, wherein the handle has a third cross-sectional area larger than the first cross-sectional area of the interior space of the retention tube to prevent the handle from completely entering into the interior space of the retention tube.

10. The device of claim 1 further comprising means for affixing a portion of the control member to maintain sealable engagement between the plug and the opening of the retention tube.

11. The device of claim 1, wherein the plug is adapted to float in said fluid.

12. The device of claim 1, wherein the plug comprises a hollow body of a first material, and a filling disposed within the hollow body of a second material less dense than the first material.

13. The device of claim 1 further comprising a support jacket partially surrounding a portion of the retention tube and configured to provide column strength to the retention tube.

14. A sampling device for sampling a fluid, the device comprising:
- a first member and a second member each having a wall defining an interior space with a first cross-sectional area, each member having an upper end and a lower end, each member being removably coupled to one another to define a retention tube having an opening to receive a sample of said fluid;
- a coupling having a first end configured to receive the upper end of the first member and a second end configured to receive the lower end of the second member;
- a control member having a proximal end and a distal end, the control member being at least partially positioned within the interior spaces of the coupled first and second members, the proximal and distal ends of the control member extending through and past the ends of the retention tube; and
- a plug coupled to the distal end of the control member, the plug being movable to a position away from the opening of the retention tube to facilitate flow of said fluid into the interior spaces of the coupled first and second members during insertion of the retention tube into said fluid, the plug comprising a portion having a second cross-sectional area larger than the first cross-sectional area of the interior spaces, the plug portion being configured to sealably engage the opening of the retention tube so that a sample of said fluid is retained within the interior spaces of the first and second members,
- wherein the control member comprises an elasticity adapted to stretch momentarily under a jolt to the retention tube to cause the plug to disengage from the opening so that a portion of the retained sample is released from the opening of the retention tube.

15. A method of obtaining a sample of a body of fluid, the method comprising:
- providing a sampling device for sampling the body of fluid, the device comprising a retention tube comprising a wall defining an interior space, the retention tube having an upper end and a lower end and an opening at the lower end to receive a sample of said fluid, a control member having a proximal end and a distal end, the control member being at least partially positioned within the interior space of the retention tube, a plug coupled to the distal end of the control member and free to float within the body of fluid to a position adjacent to the retention tube;
- lowering the device into the body of fluid, wherein the plug floats away from the opening to permit the filling of the retention tube with a sample of the body of fluid without interaction with the plug;
- applying a withdrawing force to the proximal end of the control member to sealably engage the plug with the opening of the retention tube so that the sample is retained within the retention tube; and
- lifting the device with the retained sample out of the body of fluid without disengaging the sealably engaged plug,
- wherein the control member comprises an elasticity configured to stretch momentarily under a jolt, and the method comprises jolting the retention tube with the retained sample while the plug is sealably engaged with the opening of the retention tube so that the control member is stretched momentarily to cause the plug to disengage from the opening so that a portion of the retained sample is released from the opening of the retention tube.

16. The device of claim 14, wherein the control member comprises a material selected from the group consisting of nylon, polyester, polyester/nylon combination, and polypropylene.

* * * * *